United States Patent [19]
Davis et al.

[11] Patent Number: 5,670,643
[45] Date of Patent: Sep. 23, 1997

[54] METHOD FOR PREPARING FINASTERIDE

[75] Inventors: Roman Davis, Durham; Alan Millar, Holly Springs, both of N.C.

[73] Assignee: Glaxo Wellcome Inc., Research Triangle Park, N.C.

[21] Appl. No.: 405,559

[22] Filed: Mar. 16, 1995

[51] Int. Cl.$^6$ .................................................. C07D 221/18
[52] U.S. Cl. .................................................. 546/77; 546/61
[58] Field of Search .................................................. 546/61, 77

[56] References Cited

U.S. PATENT DOCUMENTS

| | | | |
|---|---|---|---|
| 4,377,584 | 3/1983 | Rasmusson | 424/258 |
| 4,760,071 | 7/1988 | Rasmusson | 514/284 |
| 5,468,860 | 11/1995 | Dolling et al. | 546/77 |
| 5,571,817 | 11/1996 | Rasmusson et al. | 514/284 |

FOREIGN PATENT DOCUMENTS

| | | |
|---|---|---|
| 0271220 | 11/1987 | European Pat. Off. . |
| 9216213 | 10/1992 | WIPO . |

OTHER PUBLICATIONS

G. H. Rasmusson, et al., "Steroids: Structure–Activity Relationships for Inhibition of 5α-Reductase Androgen Receptor Binding," *J. Med.Chem.*, 29, pp. 2298–2315, 1986 no month available.

*Primary Examiner*—Christine Skane
*Assistant Examiner*—John R. Hardee
*Attorney, Agent, or Firm*—Robert H. Brink

[57] ABSTRACT

The present invention relates to a process for the preparation of finasteride, the compound of formula (I), comprising the reaction of the compound of formula (II) with t-butylamine.

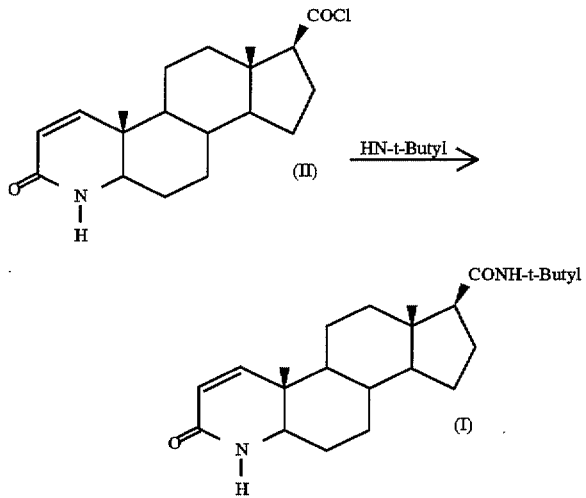

5 Claims, No Drawings

METHOD FOR PREPARING FINASTERIDE

The present invention relates to a process for the preparation of 17β-N-t butylcarbamoyl-4-aza-5α-androst-1-en-3-one, know by the generic name finasteride.

BACKGROUND OF THE INVENTION

Androgens are responsible for many physiological functions in both males and females. Androgen action is mediated by specific intracellular hormone receptors expressed in androgen responsive cells. Testosterone, the major circulating androgen, is secreted by Leydig cells of the testes under the stimulation of pituitary-derived luteinizing hormone (LH). However, reduction of the 4, 5 double bond of testosterone to dihydrotestosterone (DHT) is required in some target tissues, such as prostate and skin, for androgen action. Steroid 5α-reductases in target tissues catalyze conversion of testosterone to DHT in an NADPH dependent fashion as shown in Scheme A.

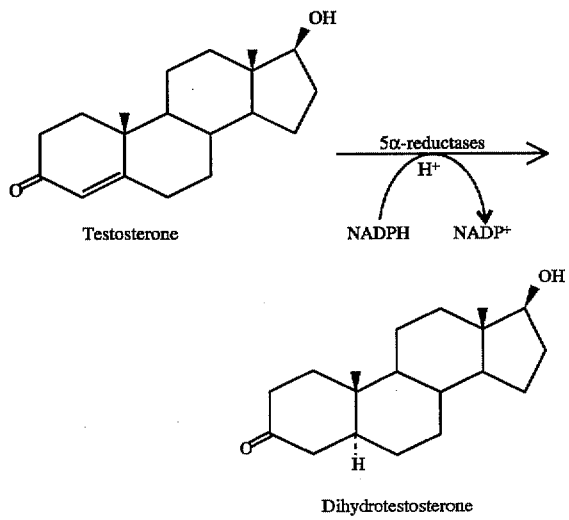

A particularly promising 5α-reductase inhibitor is 17β-N-t-butylcarbamoyl-4-aza-5α-androst-1-en-3-one, also known by the generic name finasteride and marketed by Merck under the trademark, Proscar.

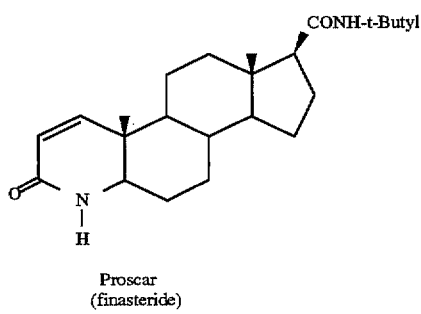

Proscar
(finasteride)

SUMMARY OF THE INVENTION

The compound of formula (II) is reacted with t-butylamine to yield the compound of formula (I), i.e., finasteride.

Scheme 1

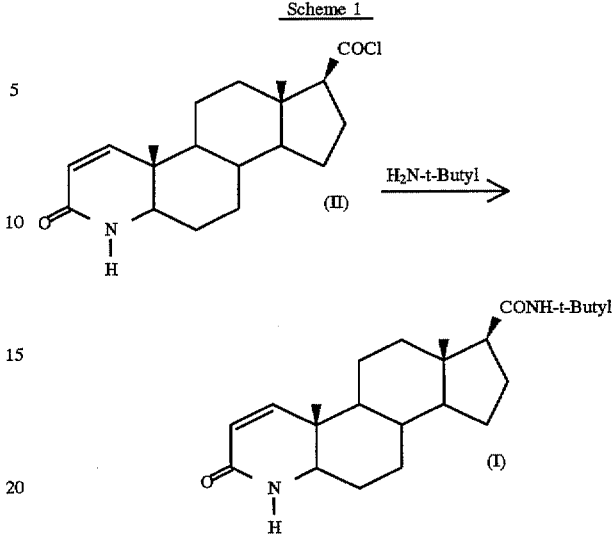

DETAILED DESCRIPTION OF THE INVENTION

In particular the process of Scheme 1 may be carried out by reacting the acid chloride of formula (II) with t-butylamine in an aprotic solvent, e.g., pyridine, toluene, methylene chloride, dimethylformamide, or acetonitrile in the presence of a base, e.g., pyridine, diisopropylethylamine dimethylaminopyridine, or triethylamine, in the temperature range of from about 20° C. to about 60° C. Those skilled in this art will appreciate that salts such as LiCl and LiBr, might be used to facilitate this reaction. The resulting compound of formula (I) may be purified by standard methods of the art such as chromatography and crystallization.

According to Scheme 2, the acid chloride of formula (II) may be prepared by reacting 3-oxo-4-aza-5α-androst-1-ene-17β-carboxylic acid of formula (III) (Rasmusson, G. H., et el., *J. Med. Chem.*, 29, 2298 (1986) and U.S. Pat. No. 4,377,584, issued Mar. 22, 1983 and incorporated herein by reference) with thionyl chloride in pyridine, toluene, methylene chloride, or acetonitrile in the presence of pyridine in the temperature range from about −10° C. to about 20° C. for from about 20 minutes to about three hours. Those skilled in this art will appreciate that addition of a catalytic amount of dimethylformamide can be used to promote the formation of the acid chloride.

Scheme 2

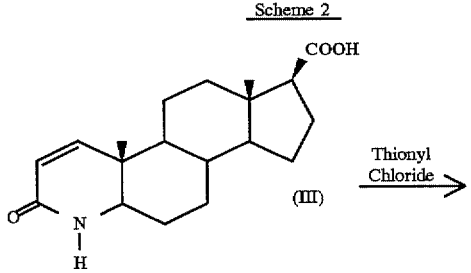

-continued
Scheme 2

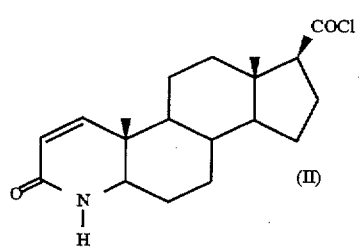

EXAMPLES

The following example illustrates this invention but should not be construed as a limitation. The symbols and conventions used in these examples are consistent with those used in the contemporary chemical literature, for example, the *Journal of the American Chemical Society*.

Example 1

17β-N-t-Butylcarbamoyl-4-aza-5α-androstat-1-en-3-one

To a solution of 3-oxo-4-aza-5α-androst-1-ene-17β-carboxylic acid (Rasmusson, G. H. et al., *J. Med. Chem.*, 29, 2298 (1986)) (1.0 g, 3.5 mmol), dry pyridine (25 mL) and dimethylformamide (20 µL) at −7° C. is added thionyl chloride (0.28 mL, 3.79 mmol). The ice bath is removed and the reaction mixture allowed to warm to room temperature. After 3 h, t-butylamine (0.66 mL, 6.3 mmol) and dimethylaminopyridine (10 mg) are added and the mixture stirred for 4–5 h, to give 17β-N-t-Butylcarbamoyl-4-aza-5α-androst-1-en-3-one as indicated by co-elution with an authentic sample of compound (I) using High Performance Liquid Chromatography.

We claim:

1. A process for preparing finasteride comprising reacting a compound of formula (II) with tertiary butylamine, wherein the acid chloride of Formula II is prepared by treating the parent acid with thionyl chloride

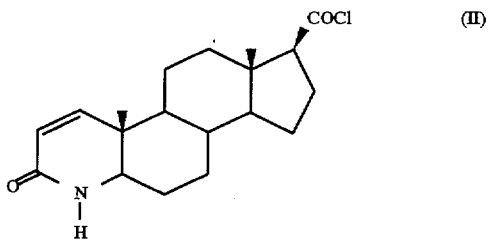

2. The process of claim 1 carried out in an aprotic solvent in the presence of a base.

3. The process of claim 2 wherein the aprotic solvent and the base is pyridine.

4. The process of claim 1 wherein said reaction with thionyl chloride is performed in the presence of a catalytic amount of dimethylformamide.

5. The method of claim 1 wherein said acid chloride is not isolated prior to said reaction with tertiary butylamine.

* * * * *